US011339352B2

(12) United States Patent
Ceulemans et al.

(10) Patent No.: US 11,339,352 B2
(45) Date of Patent: May 24, 2022

(54) ANTIMICROBIAL HARD SURFACE CLEANERS COMPRISING ALKYLPYRROLIDONES

(71) Applicant: The Procter & Gamble Company, Cincinnati, OH (US)

(72) Inventors: Raphael Angeline Alfons Ceulemans, Holsbeek (BE); Stefanos Kantaridis, Brussels (BE); Eva Maria Perez Prat Vinuesa, Newcastle upon Tyne (GB)

(73) Assignee: The Procter & Gamble Company, Cincinnati, OH (US)

( * ) Notice: Subject to any disclaimer, the term of this patent is extended or adjusted under 35 U.S.C. 154(b) by 272 days.

(21) Appl. No.: 16/387,568

(22) Filed: Apr. 18, 2019

(65) Prior Publication Data
US 2019/0330564 A1 Oct. 31, 2019

(30) Foreign Application Priority Data
Apr. 27, 2018 (EP) .................... 18169818

(51) Int. Cl.
| | |
|---|---|
| *C11D 1/62* | (2006.01) |
| *C11D 1/72* | (2006.01) |
| *C11D 1/75* | (2006.01) |
| *C11D 3/26* | (2006.01) |
| *C11D 3/37* | (2006.01) |
| *C11D 3/48* | (2006.01) |
| *C11D 1/86* | (2006.01) |
| *A01N 25/30* | (2006.01) |
| *A01N 33/12* | (2006.01) |
| *A61L 2/18* | (2006.01) |
| *C11D 1/835* | (2006.01) |
| *C11D 3/33* | (2006.01) |
| *C11D 11/00* | (2006.01) |
| *C11D 1/04* | (2006.01) |
| *C11D 1/58* | (2006.01) |

(52) U.S. Cl.
CPC ................ *C11D 1/86* (2013.01); *A01N 25/30* (2013.01); *A01N 33/12* (2013.01); *A61L 2/18* (2013.01); *C11D 1/835* (2013.01); *C11D 3/33* (2013.01); *C11D 3/3707* (2013.01); *C11D 3/3723* (2013.01); *C11D 3/48* (2013.01); *C11D 11/0023* (2013.01); *A61L 2202/17* (2013.01); *C11D 1/04* (2013.01); *C11D 1/58* (2013.01); *C11D 1/72* (2013.01); *C11D 1/75* (2013.01)

(58) Field of Classification Search
CPC .... C11D 1/62; C11D 1/72; C11D 1/75; C11D 3/26; C11D 3/3723; C11D 3/48
See application file for complete search history.

(56) References Cited

U.S. PATENT DOCUMENTS

| | | | |
|---|---|---|---|
| 5,252,245 A | 10/1993 | Garabedian, Jr. | |
| 6,211,132 B1 | 4/2001 | Pierce | |
| 9,241,483 B2 | 1/2016 | Golden | |
| 2007/0037721 A1* | 2/2007 | Michels | ........... C11D 7/265 510/295 |
| 2010/0160201 A1 | 6/2010 | Scheuing | |
| 2013/0137618 A1* | 5/2013 | Wood | ........... C11D 17/0043 510/109 |
| 2014/0004208 A1 | 1/2014 | Golden | |

FOREIGN PATENT DOCUMENTS

| | | | | |
|---|---|---|---|---|
| WO | WO 94/23003 | * | 10/1994 | ........... C11D 3/28 |
| WO | WO9423003 A1 | | 10/1994 | |
| WO | WO0250225 A1 | | 6/2002 | |
| WO | WO2004074417 A1 | | 9/2004 | |
| WO | WO02/50241 A2 | | 6/2005 | |

OTHER PUBLICATIONS

Extended European Search Report; Application No. 18169818.4-1105; dated Oct. 15, 2018; 7 pages.

* cited by examiner

*Primary Examiner* — Brian P Mruk
(74) *Attorney, Agent, or Firm* — George H. Leal

(57) ABSTRACT

The need for an antimicrobial hard surface cleaning composition which provides improved removal of greasy residues, especially greasy soap scum, is met by formulating the antimicrobial hard surface cleaning composition with an alkyl pyrrolidone surfactant and additional nonionic surfactant.

10 Claims, No Drawings

ANTIMICROBIAL HARD SURFACE CLEANERS COMPRISING ALKYLPYRROLIDONES

FIELD OF THE INVENTION

Alkaline antimicrobial hard surface cleaning compositions comprising alkyl pyrrolidones and their use in improving the removal of grease residues from surfaces while maintaining antimicrobial efficacy.

BACKGROUND OF THE INVENTION

Hard surface cleaning compositions are used for cleaning and treating hard surfaces. Preferably, the hard surface cleaning composition is formulated to be an "all purpose" hard surface cleaning composition. That is, the hard surface cleaning composition is formulated to be suitable for cleaning as many different kinds of surfaces as possible.

For treating surfaces where high levels of hygiene is desired, such as toilets, bathrooms, and surfaces that small infants can come into contact with, it is desirable that the hard surface cleaning composition comprises an anti-bacterial agent such as a quaternary ammonium compound.

Grease residues found around the home include oils and greases typically found around the kitchen, including hard to remove grease residues such as baked on (polymerized) grease. Such grease residues are more effectively removed by alkaline detergent compositions since the alkalinity leads to improved emulsification of the grease. Other grease residues found around the home include greasy soap scum which combine grease with limescale. Such greasy soap scum are less effectively removed by alkaline detergent compositions and typically have required acid detergent compositions to dissolve the limescale so that the grease can be removed. Detersive surfactants, especially nonionic detersive surfactants, are added to improve grease removal. However, such detersive surfactants have a tendency to "capture" the antimicrobial active in micelles. Hence, the addition of detersive surfactants tends to reduce the efficacy of the antimicrobial active. Moreover, since the antimicrobial active stabilizes the detersive surfactant micelle, the grease cleaning efficacy of the detersive surfactant is also reduced. Hence, such antimicrobial agents can inhibit the cleaning efficacy of surfactants, leading to less than ideal cleaning, especially grease cleaning, and less than ideal shine.

As such, a need remains for a hard surface cleaning composition which provides good antimicrobial efficacy, in addition to improved removal of a broad range of grease residues.

WO2004/074417 relates to aqueous acidic antimicrobial compositions comprising acid, an amine oxide surfactant, and an N-alkylpyrrolidone derivative. WO2002/50225 relates to aqueous acidic antimicrobial compositions comprising surfactant, acid, an N-alkylpyrrolidone derivative, and a co-solvent. WO2002050241 relates to antimicrobial wipes which comprise a substrate incorporating an aqueous surfactant composition and an N-alkylpyrrolidone derivative. U.S. Pat. No. 9,241,483 relates to disinfectant compositions comprising a peroxide, peracid, anionic surfactant, nonionic polymer, linear fatty alcohol and an alkyl pyrrolidone.

EP 0 580 838 81 A relates to aqueous hard surface cleaners which comprise (a) an effective amount of a solvent selected from C1-6 alkanol, C3-24 alkylene glycol ether and mixtures (B) an effective amount of a surfactant selected from amphoteric, nonionic and anionic surfactants and mixtures of said surfactants, (c) an effective amount of a buffer system which comprises a nitrogen buffer selected from the group consisting of carbamates of ammonium or of alkaline earths, derivatives of guanidine, alkoxyalkylamines and alkyleneamines; and (d) the remainder consisting substantially of water.

SUMMARY OF THE INVENTION

The present invention relates to an antimicrobial liquid hard surface cleaning composition comprising: an alkylpyrrolidone surfactant; additional nonionic surfactant; and an antimicrobial agent; wherein the liquid hard surface cleaning composition has a pH of greater than 4.0.

DETAILED DESCRIPTION OF THE INVENTION

The alkaline hard surface cleaning compositions of the present invention, provide good antimicrobial efficacy, in addition to improved removal of a broad range of grease residues, especially greasy soap scum.

As defined herein, "essentially free of" a component means that no amount of that component is deliberately incorporated into the respective premix, or composition. Preferably, "essentially free of" a component means that no amount of that component is present in the respective premix, or composition.

As used herein, "isotropic" means a clear mixture, having little or no visible haziness, phase separation and/or dispersed particles, and having a uniform transparent appearance.

As defined herein, "stable" means that no visible phase separation is observed for a premix kept at 25° C. for a period of at least two weeks, or at least four weeks, or greater than a month or greater than four months, as measured using the Floc Formation Test, described in USPA 2008/0263780 A1.

All percentages, ratios and proportions used herein are by weight percent of the premix, unless otherwise specified. All average values are calculated "by weight" of the premix, unless otherwise expressly indicated.

All measurements are performed at 25° C. unless otherwise specified.

Unless otherwise noted, all component or composition levels are in reference to the active portion of that component or composition, and are exclusive of impurities, for example, residual solvents or by-products, which may be present in commercially available sources of such components or compositions.

Antimicrobial Liquid Hard Surface Cleaning Compositions:

By "liquid hard surface cleaning composition", it is meant herein a liquid composition for cleaning hard surfaces found in households, especially domestic households. Surfaces to be cleaned include kitchens and bathrooms, e.g., floors, walls, tiles, windows, cupboards, sinks, showers, shower plastified curtains, wash basins, WCs, fixtures and fittings and the like made of different materials like ceramic, vinyl, no-wax vinyl, linoleum, melamine, glass, steel, kitchen work surfaces, any plastics, plastified wood, metal or any painted or varnished or sealed surface and the like. Household hard surfaces also include household appliances including, but not limited to refrigerators, freezers, washing machines, automatic dryers, ovens, microwave ovens, dishwashers and so on. Such hard surfaces may be found both in private households as well as in commercial, institutional and industrial environments.

In a preferred embodiment, the liquid compositions herein are aqueous compositions. Therefore, they may comprise from 30% to 99.5% by weight of the total composition of water, preferably from 50% to 98% and more preferably from 80% to 97%.

The compositions of the present invention preferably have a viscosity from 1 cps to 650 cps, more preferably of from 100 cps to 550 cps, more preferably from 150 cps to 450 cps, even more preferably from 150 cps to 300 cps and most preferably from 150 cps to 250 cps when measured at 20° C. with a AD1000 Advanced Rheometer from Atlas® shear rate $10\ s^{-1}$ with a coned spindle of 40 mm with a cone angle 2° and a truncation of ±60 am.

Greasy soap scum comprises, amongst other ingredients, limescale and soap. Such greasy residues are particularly hard to remove since the limescale forms a water-impermeable barrier which makes the greasy soap scum difficult to remove. As such, hard surface cleaning compositions for removing greasy soap scum have typically been formulated with a pH of less than 4.0 and more typically less than 3, in order to dissolve the limescale contained within the greasy soap scum. However, in order to improve grease removal efficacy, an alkaline pH is highly desired since the hydrolysis (saponification), chelation and dispersion of soils is improved at highly alkaline pH. It has surprisingly been found that the compositions, comprising the alkylpyrrolidone surfactant, improve the removal of greasy residues, even greasy soap scum, and even when formulated into compositions having a lightly acidic or weakly alkaline pH. As such, the pH is greater than 4.0, preferably from 4.0 to 13, more preferably from 7.5 to 11.5, even more preferably from 9.5 to 11.3, most preferably 10 to 11, measured on the neat composition, at 25° C. It is also believed that the greasy soil and particulate greasy soil cleaning performance is further improved at these preferred alkaline pH ranges. Accordingly, the compositions herein may further comprise an acid or base to adjust pH as appropriate.

A suitable acid of use herein is an organic and/or an inorganic acid. A preferred organic acid of use herein has a pKa of less than 6. A suitable organic acid is selected from the group consisting of: citric acid, lactic acid, glycolic acid, succinic acid, glutaric acid and adipic acid and mixtures thereof. A suitable inorganic acid can be selected from the group consisting of: hydrochloric acid, sulphuric acid, phosphoric acid and mixtures thereof.

A typical level of such acids, when present, is from 0.01% to 5.0% by weight of the total composition, preferably from 0.04% to 3.0% and more preferably from 0.05% to 1.5%.

A suitable base to be used herein is an organic and/or inorganic base. Suitable bases of use herein are the caustic alkalis, such as sodium hydroxide, potassium hydroxide and/or lithium hydroxide, and/or the alkali metal oxides such, as sodium and/or potassium oxide or mixtures thereof. A preferred base is a caustic alkali, more preferably sodium hydroxide and/or potassium hydroxide.

Other suitable bases include $K_2CO_3$, $Na_2CO_3$, bicarbonates (such as ammonium bicarbonate or sodium bicarbonate), and nitrogeneous bases. Suitable nitrogenous bases include those selected from the group consisting of: ammonium hydroxide (or ammonia which forms ammonium hydroxide in situ when added to aqueous compositions), ammonium carbonate, alkanolamines (such as monoethanolamine, triethanolamine, aminomethylpropanol, and mixtures thereof), carbamates (such as ammonium, alkaline earth carbamates, and mixtures thereof), guanidine derivatives (such as 1,1,3,3-tetramethylguanidine, triazabicyclodecene, and mixtures thereof), and mixtures thereof. Alkanolamines such as monoethanolamine, triethanolamine, aminomethylpropanol, and mixtures thereof, are particularly preferred, especially monoethanolamine, triethanolamine, and mixtures thereof, more especially monoethanolamine.

Typical levels of such bases, when present, are from 0.01% to 5.0% by weight of the total composition, preferably from 0.05% to 3.0% and more preferably from 0.1% to 2.0%.

Surfactant System:

The antimicrobial liquid hard surface cleaning composition comprises a surfactant system, the surfactant system comprising an alkyl pyrrolidone; and an additional nonionic surfactant, in addition to the antimicrobial agent.

Alkyl Pyrrolidone:

Pyrrolidone-based surfactants, including alkyl pyrrolidones, are well known and their use and methods of making them have been extensively reviewed (for instance in Pyrrolidone-based surfactants (a literature review), Login, R. B. J Am Oil Chem Soc (1995) 72: 759-771). Such alkyl pyrrolidones have been found to provide improved grease removal, especially greasy soap scum removal as well as water-mark removal, even when used in the antimicrobial hard surface cleaning compositions of the present invention, while maintaining antimicrobial efficacy.

Suitable alkyl pyrrolidones can have the formula:

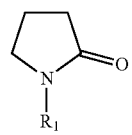

wherein $R_1$ is C6-C20 alkyl, or $R_2NHCOR_3$, and $R_2$ is C1-6 alkyl and $R_3$ is C6-20 alkyl. R1 is preferably C6-C20 alkyl. N-alkyl pyrrolidones are particularly suitable for use in compositions of the present invention, with N-alkyl-2-pyrrolidones being particularly suited. Suitable alkylpyrrolidones include N-alkyl-2-pyrrolidones, wherein the alkyl chain is C6 to C20, or C6 to C10, or C8. N-octyl-2-pyrrolidone is particularly preferred for their efficacy in removing limescale based stains, even when used in alkaline compositions. The alkyl chain can be substituted, though unsubstituted alkyl pyrrolidones are preferred. The alkyl chain is preferably fully saturated.

The alkyl pyrrolidone can be present at a level of from 0.1 to 10%, preferably from 0.25 to 8.0, more preferably from 0.5 to 5.0% and most preferably from 1.0 to 3.0% by weight of the composition.

Suitable alkyl pyrrolidones are marketed under the tradename Surfadone® by the Ashland Inc., such as Surfadone LP-100 (N-octly-2-pyrrolidone) and LP-300 (N-docedycl-2-pyrrolidone), and is also available from BASF.

Additional Nonionic Surfactant

The antimicrobial liquid hard surface cleaning composition comprises an additional nonionic surfactant. The additional nonionic surfactant can be selected from the group consisting of: alkoxylated nonionic surfactants, alkyl polyglycosides, amine oxides, and mixture thereof. More preferably, the additional nonionic surfactant can be selected from the group consisting of: alkoxylated nonionic surfactants, amine oxide nonionic surfactant, and mixtures thereof.

Most preferably, the nonionic surfactant comprises a combination of alkoxylated nonionic surfactants and amine oxide nonionic surfactant.

Typically, the antimicrobial liquid hard surface cleaning composition may comprise the additional nonionic surfactant at a level of from 0.3% to 12%, preferably from 0.5% to 9.5%, more preferably from 3.0% to 8.0% by weight of the composition.

The weight ratio of nonionic surfactant to alkylpyrrolidone in the composition can be from 140:1 to 0.10:1, preferably from 48:1 to 0.25:1, more preferably from 20:1 to 0.60:1 and most preferably from 8.0:1 to 1.33:1. Such compositions provide improved grease removal, especially greasy soap scum removal.

The hard surface cleaning composition can comprise from 0.27% to 8.0%, preferably from 0.45% to 6.5%, more preferably from 2.9% to 6.0% by weight of the composition of alkoxylated nonionic surfactant, preferably ethoxylated alcohol.

Suitable alkoxylated nonionic surfactants include primary $C_6$-$C_{16}$ alcohol polyglycol ether i.e. ethoxylated alcohols having 6 to 16 carbon atoms in the alkyl moiety and 4 to 30 ethylene oxide (EO) units. When referred to for example $C_{9-14}$ it is meant average carbons and alternative reference to for example EO8 is meant average ethylene oxide units.

Suitable alkoxylated nonionic surfactants are according to the formula RO-(A)$_n$H, wherein: R is a $C_6$ to $C_{18}$, preferably a $C_8$ to $C_{16}$, more preferably a $C_8$ to $C_{12}$ alkyl chain, or a $C_6$ to $C_{28}$ alkyl benzene chain; A is an ethoxy or propoxy or butoxy unit, and wherein n is from 1 to 30, preferably from 1 to 15 and, more preferably from 4 to 12 even more preferably from 5 to 10. Preferred R chains of use herein are the $C_8$ to $C_{22}$ alkyl chains. Even more preferred R chains of use herein are the $C_9$ to $C_{12}$ alkyl chains. R can be linear or branched alkyl chain.

Suitable ethoxylated nonionic surfactants of use herein are Dobanol® 91-2.5 (HLB=8.1; R is a mixture of $C_9$ and $C_{11}$ alkyl chains, n is 2.5), Dobanol® 91-10 (HLB=14.2; R is a mixture of $C_9$ to $C_{11}$ alkyl chains, n is 10), Dobanol® 91-12 (HLB=14.5; R is a mixture of $C_9$ to $C_{11}$ alkyl chains, n is 12), Greenbentine DE80 (HLB=13.8, 98 wt % C10 linear alkyl chain, n is 8), Marlipal 10-8 (HLB=13.8, R is a C10 linear alkyl chain, n is 8), Lialethl® 11-5 (R is a $C_{11}$ alkyl chain, n is 5), Isalchem® 11-5 (R is a mixture of linear and branched C11 alkyl chain, n is 5), Lialethl® 11-21 (R is a mixture of linear and branched $C_{11}$ alkyl chain, n is 21), Isalchem® 11-21 (R is a $C_1$ branched alkyl chain, n is 21), Empilan® KBE21 (R is a mixture of $C_{12}$ and $C_{14}$ alkyl chains, n is 21) or mixtures thereof. Preferred herein are Dobanol® 91-5, Neodol® 11-5, Lialethl® 11-21 Lialethl® 11-5 Isalchem® 11-5 Isalchem® 11-21 Dobanol® 91-8, or Dobanol® 91-10, or Dobanol® 91-12, or mixtures thereof. These Dobanol®/Neodol® surfactants are commercially available from SHELL. These Lutensol® surfactants are commercially available from BASF and these Tergitol® surfactants are commercially available from Dow Chemicals.

Suitable chemical processes for preparing the alkoxylated nonionic surfactants of use herein include condensation of corresponding alcohols with alkylene oxide, in the desired proportions. Such processes are well known to the person skilled in the art and have been extensively described in the art, including the OXO process and various derivatives thereof. Suitable alkoxylated fatty alcohol nonionic surfactants, produced using the OXO process, have been marketed under the tradename NEODOL® by the Shell Chemical Company. Alternatively, suitable alkoxylated nonionic surfactants can be prepared by other processes such as the Ziegler process, in addition to derivatives of the OXO or Ziegler processes.

Preferably, said alkoxylated nonionic surfactant is a $C_{9-11}$ EO5 alkylethoxylate, $C_{12-14}$ EO5 alkylethoxylate, a $C_{11}$ EO5 alkylethoxylate, $C_{12-14}$ EO21 alkylethoxylate, or a $C_{9-11}$ EO8 alkylethoxylate or a mixture thereof. Most preferably, said alkoxylated nonionic surfactant is a $C_{11}$ EO5 alkylethoxylate or a $C_{9-11}$ EO8 alkylethoxylate or a mixture thereof.

Alkyl polyglycosides are biodegradable nonionic surfactants which are well known in the art. Suitable alkyl polyglycosides can have the general formula $C_nH_{2n+1}O(C_6H_{10}O_5)_xH$ wherein n is preferably from 9 to 16, more preferably 11 to 14, and x is preferably from 1 to 2, more preferably 1.3 to 1.6. Such alkyl polyglycosides provide a good balance between anti-foam activity and detergency. Alkyl polyglycoside surfactants are commercially available in a large variety. An example of a very suitable alkyl poly glycoside product is Planteren APG 600, which is essentially an aqueous dispersion of alkyl polyglycosides wherein n is about 13 and x is about 1.4.

Suitable amine oxide surfactants include: $R_1R_2R_3NO$ wherein each of $R_1$, $R_2$ and $R_3$ is independently a saturated or unsaturated, substituted or unsubstituted, linear or branched hydrocarbon chain having from 10 to 30 carbon atoms. Preferred amine oxide surfactants are amine oxides having the following formula: $R_1R_2R_3NO$ wherein $R_1$ is an hydrocarbon chain comprising from 1 to 30 carbon atoms, preferably from 6 to 20, more preferably from 8 to 16 and wherein $R_2$ and $R_3$ are independently saturated or unsaturated, substituted or unsubstituted, linear or branched hydrocarbon chains comprising from 1 to 4 carbon atoms, preferably from 1 to 3 carbon atoms, and more preferably are methyl groups. $R_1$ may be a saturated or unsaturated, substituted or unsubstituted linear or branched hydrocarbon chain.

A highly preferred amine oxide is $C_{12}$-$C_{14}$ dimethyl amine oxide, commercially available from Albright & Wilson, $C_{12}$-$C_{14}$ amine oxides commercially available under the trade name Genaminox® LA from Clariant or AROMOX® DMC from AKZO Nobel.

Preferably, the antimicrobial liquid hard surface cleaning composition comprises from 0.03% to 4.0%, preferably from 0.05% to 3.0%, more preferably from 0.1% to 2.0% by weight of the composition of amine oxide surfactant.

The nonionic surfactant is preferably a low molecular weight nonionic surfactant, having a molecular weight of less than 950 g/mol, more preferably less than 500 g/mol.

Anionic Surfactant:

Antimicrobial agents typically interact with anionic surfactants, resulting in less antimicrobial efficacy and more residue on the treated surface (and hence less shine), the antimicrobial liquid hard surface cleaning compositions described herein preferably comprise limited amounts, or no anionic surfactant, with the exception of polycarboxylated anionic surfactants.

The antimicrobial hard surface cleaning composition preferably comprises anionic surfactant, other than polycarboxylated anionic surfactant, at a level of up to 2.0 wt %, preferably up to 1.0 wt %, or up to 0.1 wt % of anionic surfactant. In most preferred embodiments, the composition is essentially free, or free of, of anionic surfactant other than polycarboxylated anionic surfactant.

Polycarboxylated anionic surfactants have surprisingly been found to interact less with the antimicrobial agent, resulting in reduced reduction in antimicrobial efficacy and improved shine of the treated surface. As such, the antimicrobial hard surface cleaning composition can comprise anionic surfactant selected from the group consisting of polycarboxylated anionic surfactants, and mixtures thereof. Suitable polycarboxylated anionic surfactants can be selected from the group consisting of: polyalkoxylate polycarboxylated surfactants, and mixtures thereof.

The antimicrobial hard surface cleaning composition can comprise polycarboxylated anionic surfactant at a level of from 0.05% to 5%, preferably from 0.1% to 4%, most preferably from 0.25% to 2.5% by weight of the composition.

Suitable polycarboxylated anionic surfactants are described in U.S. Pat. No. 5,376,298, EP0129328, WO03018733, and U.S. Pat. No. 5,120,326. Particularly preferred are polyalkoxylate polycarboxylate surfactant, for instance, as described from column 3, line 30 to column 4, line 34 of U.S. Pat. No. 5,376,298.

Suitable polyalkoxylate polycarboxylated surfactant can have the empirical formula:

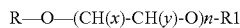

R—O—(CH($x$)-CH($y$)-O)$n$-R1 wherein R is a hydrophobic group, preferably a substituted, or unsubstituted, hydrocarbon group typically containing from 6 to 16 carbon atoms, preferably from 8 to 14 carbon atoms, x and y are each independently selected from the group consisting of hydrogen, methyl, and succinic acid radicals, with the proviso that at least one x or y moiety per molecule is a succinic acid radical, wherein n is between 1 and 60, and wherein R1 is hydrogen, substituted hydrocarbon, unsubstituted hydrocarbon preferably having between 1 and 8 carbon atoms, sulfuric, or sulfonic radical, with any acid groups being neutralized by compatible cationic groups, e.g., sodium, potassium, alkanolammonium, magnesium, etc.

Suitable polyalkoxylate polycarboxylates surfactant can have the empirical formula:

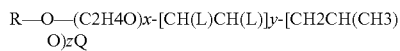

R—O—(C2H4O)$x$-[CH(L)CH(L)]$y$-[CH2CH(CH3)O]$z$Q wherein R is a hydrocarbon hydrophobic group, preferably alkyl, containing from 6 to 16, preferably from 8 to 14 carbon atoms; x is a number from 0 to 60, preferably from 4 to 50, more preferably from 6 to 50; L is either a C1-3 alkyl group or a group having the formula —CH—(COO—)CH2(COO—), with at least one L group in each molecule being —CH(COO—)CH2(COO—); y is a number from 1 to 12, preferably from 2 to 10, more preferably from 3 to 8; z is a number from 0 to 20, preferably from 0 to 15, more preferably from 0 to 10; and Q is selected from the group consisting of H and sulfonate groups, the compound being rendered electrically neutral by the presence of cationic groups, preferably selected from the group consisting of sodium, potassium, and substituted ammonium, e.g., monoethanol ammonium, cations. Specific examples of such polyalkoxylate polycarboxylate surfactant include the following: Poly-Tergent® C9-51B (CS-1) (x=12; y=8; and Z=17); Poly-Tergent® C9-62P (x=4; y=3; and z=17); Poly-Tergent® C9-74P (x=10; y=3.5; and Z=3 5.); and Poly-Tergent® C9-92 (x=approximately 55; y=6.5; and z=0). R is believed to be an alkyl group such as a linear C9 alkyl group, and Q is believed to be H. The Poly-Tergent® surfactants are now sold under the Plurafac® trade name by BASF.

Suitable polycarboxylated anionic surfactants include alkoxylated polymer, alkyl ether, alkenedioic acid salts, for instance, as sold those under the Plurafac™ CS-10 tradename by BASF.

Additional Surfactant:

The hard surface cleaning composition may comprise up to 15% by weight of an additional surfactant, preferably selected from: an amphoteric, zwitterionic, and mixtures thereof. The hard surface cleaning composition can comprise from 0.5% to 5%, or from 0.5% to 3%, or from 0.5% to 2% by weight of the additional surfactant.

Suitable zwitterionic surfactants typically contain both cationic and anionic groups in substantially equivalent proportions so as to be electrically neutral at the pH of use. The typical cationic group is a quaternary ammonium group, other positively charged groups like phosphonium, imidazolium and sulfonium groups can be used. The typical anionic hydrophilic groups are carboxylates and sulfonates, although other groups like sulfates, phosphonates, and the like can be used.

Some common examples of zwitterionic surfactants (such as betaine/sulphobetaine surfacants) are described in U.S. Pat. Nos. 2,082,275, 2,702,279 and 2,255,082. For example Coconut dimethyl betaine is commercially available from Seppic under the trade name of Amonyl 265®. Lauryl betaine is commercially available from Albright & Wilson under the trade name Empigen BB/L®. A further example of betaine is Lauryl-iminodipropionate commercially available from Rhodia under the trade name Mirataine H2C-HA®.

Sulfobetaine surfactants are particularly preferred, since they can improve soap scum cleaning. Examples of suitable sulfobetaine surfactants include tallow bis(hydroxyethyl) sulphobetaine, cocoamido propyl hydroxy sulphobetaines which are commercially available from Rhodia and Witco, under the trade name of Mirataine CBS® and ReWoteric AM CAS 15® respectively.

Amphoteric surfactants can be either cationic or anionic depending upon the pH of the composition. Suitable amphoteric surfactants include dodecylbeta-alanine, N-alkyltaurines such as the one prepared by reacting dodecylamine with sodium isethionate, as taught in U.S. Pat. No. 2,658,072, N-higher alkylaspartic acids such as those taught in U.S. Pat. No. 2,438,091, and the products sold under the trade name "Miranol", as described in U.S. Pat. No. 2,528,378. Other suitable additional surfactants can be found in McCutcheon's Detergents and Emulsifers, North American Ed. 1980.

Antimicrobial Agent:

Suitable antimicrobial agents include antimicrobial agents selected from the group consisting of: quaternary ammonium compound, and mixtures thereof.

The antimicrobial agent is required to be present in amounts which are effective in exhibiting satisfactory germicidal activity—against selected bacteria sought to be treated by the cleaning compositions. Such efficacy may be achieved against less resistant bacterial strains with only minor amounts of the quaternary ammonium compounds being present, while more resistant strains of bacteria require greater amounts of the quaternary ammonium compounds in order to destroy these more resistant strains.

The antimicrobial agent need only be present in germicidally effective amounts, which can be as little as 0.001 wt %. In more preferred compositions, the antimicrobial hard surface cleaning composition comprises the antimicrobial agent at a level of from 0.01 to 2.0%, preferably from 0.05% to 1.6%, more preferably from 0.1% to 1.2%, most preferably from 0.25% to 0.9% by weight of the composition. A germicidally effective amount of the antimicrobial agent can be considered to result in at least a log 4.5, preferably at least a log 5 reduction of *Staphylococcus aureus*, using the method of EN1276 (Chemical Disinfectants Bactericidal Activity Testing), in less than 3 minutes.

Suitable quaternary ammonium compounds are those of the formula:

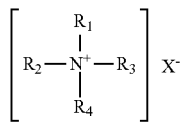

wherein at least one of $R_1$, $R_2$, $R_3$ and $R_4$ is a hydrophobic, aliphatic, aryl aliphatic or aliphatic 30 aryl radical of from 6 to 26 carbon atoms, and the entire cation portion of the molecule has a molecular weight of at least 165. The hydrophobic radical-s may be long-chain alkyl, long-chain alkoxy aryl, long-chain alkyl aryl, halogen-substituted long-chain alkyl aryl, long-chain alkyl phenoxy alkyl, aryl alkyl, etc. The remaining radicals on the nitrogen atoms other than the hydrophobic radicals are substituents of a hydrocarbon structure usually containing a total of no more than 12 carbon atoms. The radicals $R_1$, $R_2$, $R_3$ and $R_4$ may be straight chained or may be branched, but are preferably straight chained, and may include one or more amide or ester linkages. The radical X may be any salt-forming anionic radical, and preferably aids in the solubilization of the quaternary ammonium germicide in water. X can be a halide, for example a chloride, bromide or iodide, or X can be a methosulfate counterion, or X can be a carbonate ion.

Exemplary quaternary ammonium compounds include the alkyl ammonium halides such as cetyl trimethyl ammonium bromide, alkyl aryl ammonium halides such as octadecyl dimethyl benzyl ammonium bromide, N-alkyl pyridinium halides such as N-cetyl pyridinium bromide, and the like. Other suitable types of quaternary ammonium compounds include those in which the molecule contains either amide or ester linkages such as octyl phenoxy ethoxy ethyl dimethyl benzyl ammonium chloride, N-(laurylcocoaminoformylmethyl)-pyridinium chloride, and the like. Other very effective types of quaternary ammonium compounds which are useful as germicides include those in which the hydrophobic radical is characterized by a substituted aromatic nucleus as in the case of lauryloxyphenyltrimethyl ammonium chloride, cetylaminophenyltrimethyl ammonium methosulfate, dodecylphenyltrimethyl ammonium methosulfate, dodecylbenzyltrimethyl ammonium chloride, chlorinated dodecylbenzyltrimethyl ammonium chloride, and the like.

More preferred quaternary ammonium compounds used in the compositions of the invention include those of the structural formula:

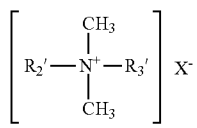

wherein $R_2'$ and $R_3'$ may be the same or different and are selected from C8-C12 alkyl, or $R_2'$ is C12-C16 alkyl, C8-C18 alkylethoxy, C8-C18 alkylphenolethoxy and $R_3'$ is benzyl, and X is a halide, for example a chloride, bromide or iodide, or X is a methosulfate counterion. The alkyl groups recited in $R_2'$ and $R_3'$ may be linear or branched, but are preferably substantially linear, or fully linear.

Particularly useful quaternary germicides include compositions presently commercially available under the tradenames BARDAC, and BARQUAT. These quaternary ammonium compounds are usually provided in a solvent, such as a C2 to C6 alcohol (such as ethanol, n-propanol, isopropanol, n-butanol, sec-butanol, and the like), glycols such as ethylene glycol, or in an mixtures containing water, such alcohols, and such glycols. Particularly preferred is didecyl dimethyl ammonium chloride, such as supplied by Lonza under tradenames such as: Bardac 2250™, Bardac 2270™, Bardac 2270E™, Bardac 2280™, and/or a blend of alkyl, preferably C12-C18, dimethyl benzyl ammonium chloride and alkyl, preferably C12-C18, dimethyl ethylbenzyl ammonium chloride, such as supplied by Lonza under the brand names: Barquat 4280Z™. In preferred embodiments, the alkyl dimethyl benzyl ammonium chloride and alkyl dimethyl ethylbenzyl ammonium chloride are present in a ratio of from 20:80 to 80:20, or 40:60 to 60:40, with a ratio of 50:50 being the most preferred.

Optional Ingredients:

Thickener:

The antimicrobial liquid hard surface cleaning composition can comprise a thickener. An increased viscosity, especially low shear viscosity, provides longer contact time and therefore improved penetration of greasy soil and/or particulated greasy soil to improve cleaning effectiveness, especially when applied neat to the surface to be treated. Moreover, a high viscosity improves the contact time for the hard surface cleaning composition on inclined surfaces. The alkyl pyrrolidones of use in the present invention have been found to improve the viscosity of thickened hard surface cleaning compositions, and are hence particularly suited for cleaning inclined surfaces. Hence, the antimicrobial liquid hard surface cleaning composition can comprise a thickener, to provide a viscosity of from 50 Pa·s to 650 Pa·s, more preferably 100 Pa·s to 550 Pa·s, most preferably 150 Pa·s to 450 Pa·s, at 20° C. when measured with a AD1000 Advanced Rheometer from Atlas® shear rate 10 s$^{-1}$ with a coned spindle of 40 mm with a cone angle 2° and a truncation of ±60 am.

Suitable thickeners include polyacrylate based polymers, preferably hydrophobically modified polyacrylate polymers; hydroxyl ethyl cellulose, preferably hydrophobically modified hydroxyl ethyl cellulose, xanthan gum, and mixtures thereof.

Preferred thickeners are polyacrylate based polymers, preferably hydrophobically modified polyacrylate polymers. Preferably a water-soluble copolymer based on main monomers acrylic acid, acrylic acid esters, vinyl acetate, methacrylic acid, acrylonitrile and mixtures thereof, more preferably copolymer is based on methacrylic acid and acrylic acid esters having appearance of milky, low viscous dispersion. Most preferred hydrologically modified polyacrylate polymer is Rheovis® AT 120, which is commercially available from BASF.

Other suitable thickeners are hydroxethylcelluloses (HM-HEC) preferably hydrophobically modified hydroxyethylcellulose. Suitable hydroxyethylcelluloses (HM-HEC) are commercially available from Aqualon/Hercules under the product name Polysurf 76® and W301 from 3V Sigma.

Xanthan gum is one suitable thickener used herein. Xanthan gum is a polysaccharide commonly used rheoligy modifier and stabilizer. Suitable Xanthan gum is commercially available under trade anem Kelzan T® from CP Kelco.

When used, the antimicrobial liquid hard surface cleaning composition comprises from 0.1% to 10.0% by weight of the total composition of said thickener, preferably from 0.2% to 5.0%, more preferably from 0.2% to 2.5% and most preferably from 0.2% to 2.0%.

Chelating Agent:

The antimicrobial liquid hard surface cleaning composition can comprise a chelating agent or crystal growth inhibitor. Suitable chelating agents, in combination with the surfactant system, improve the shine benefit. The addition of a chelant, especially chelants selected from the group consisting of: amino-carboxylates (such as diethylenetriaminepentaacetic acid [DTPA]), carboxylated fructan, phosphonate chelating agents, and mixtures thereof, preferably carboxylated fructan, phosphonate chelating agents, and mixtures thereof, more preferably carboxylated fructan, surprisingly further improve greasy soap scum and water-mark removal as well as shine from the treated surface.

Chelating agent can be incorporated into the compositions in amounts ranging from 0.025% to 5.0% by weight of the total composition, preferably from 0.15% to 4.0%, more preferably from 0.2% to 3.0% and most preferably from 0.3% to 2.0%, or even from 1.0% to 2.0%.

Fructans are described in S. Mitmesser and M. Combs, "Prebiotics: Inulin and Other Oligosaccharides", Ch 23, part C (Food Substrates Important to the Microbiota), The Microbiota in Gastrointestinal Pathophysiology, Academiuc Press, 2017. Fructans are a group of oligo- and polysaccharides composed of fructose units connected with β-(2→1) linkages, and frequently terminating in a glucosyl moiety (as described in Roberfroid M B, Van Loo J A, Gibson G R, "The bifidogenic nature of chicory inulin and its hydrolysis products.", J Nutr 1998; 128(1):11-9). The shortest members of this structural classification are called oligofructose (or FOS), and consist of 2-9 units, while fructans with 10 or more monomeric units are typically categorized as inulin. The number of units in a polysaccharide chain is also frequently referred to as degrees of polymerization (DP).

Many plants store carbohydrates in the form of inulin. Globe and Jerusalem artichokes, chicory, and agave are plants used for the commercial extraction of inulin, but other foods, such as wheat, bananas, onions, and garlic also contain inulin. Fructans can also be enzymatically synthesized from sucrose via transfructosylation. Chicory inulin is typically a linear beta (2->1) fructan (typically having a degree of polymerisation (DP) 2 to 60, with an average DP of typically 12.

Suitable carboxylated fructan include those described in WO2010106077 A as "component (II)", such as carboxylated fructan selected from the group consisting of: carboxyalkylfructan, preferably carboxyalkylinulin, having from 1 to 4 carbon atoms in the alkyl moiety; dicarboxyfructan having a degree of oxidation (DO) of from 10 to 100%, preferably 20 to 90%, expressed as a molar percentage of monosaccharide units converted into the corresponding dicarboxy analogues; 6-carboxyfructan, preferably 6-carboxyinulin; fructan polycarboxylic acid, preferably inulin polycarboxylic acid, having a degree of carboxyalkylation or carboxyacylation of from 0.2 to 3.0; and mixtures thereof.

Fructans used as starting material for producing the carboxylated fructans can be oligo- and polysaccharides which have a majority of anhydrofructose units, and can have a polydisperse chain length distribution and can be of straight- or branched-chain. Preferably the fructan contains mainly beta-2.1 bonds, as in inulin. The fructans used as starting material can be products obtained directly from a vegetable source or other sources as well as products in which the average chain length has been modified, increased or reduced, by fractionation, enzymatic synthesis or hydrolysis.

Carboxylated fructans with modified average chain length can be made from fructans with enzymatically increased chain length, fructanhydrolysis products having shortened chains and fractionated products having a modified chain length. Fractionating of fructans such as inulin can be achieved, for example, by means of known techniques including low temperature crystallization (see WO 96/01849), column chromatography (see WO 94/12541), membrane filtration (see EP-A-0440074, EP-A-0627490) or selective precipitation with alcohol. Hydrolysis to yield shorter fructans can be carried out, for example, enzymatically (endo-insulase), chemically (water and acid) or by heterogeneous catalysis (acid column). Reduced, oxidized, hydroxyalkylated and/or crosslinked fructans can also represent suitable starting materials to produce the carboxylated fructans. The fructans can have an average chain length (degree of polymerization, DP) of at least 3 to about 1000. Preferably, the average chain length is from 3 to 60, in particular of from 5 to 30 monosaccharide units. A preferred fructan is inulin (beta-2, 1-fructan) or a modified inulin.

Particularly suited fructan include carboxymethylinulin and/or carboxyethylinulin, preferably with a degree of substitution (DS) in the range of from 1.5 to 2.8, and/or dicarboxyinulin having a degree of oxidation (DO) of from 20 to 90%, expressed as a molar percentage of monosaccharide units converted into the corresponding dicarboxy analogues.

Carboxymethylinulin can be prepared by reaction of the fructan with chloroacetic acid as described in WO95/15984. Carboxylethylinulin can be prepared in accordance with the method of WO 96/34017. The carboxyalkylinulin so prepared can have a degree of substitution (DS) up to 3.0. The DS of such carboxyalkylinulins is generally within the range of from 0.2 to 3.0, preferably from 1.0 to 2.8. Preferred carboxy alkylinulins have a DS in the range of from 1.5 to 2.8, most preferably 1.8 to 2.5.

Dicarboxyinulins can be obtained through oxidation of the inulin raw material. The anhydrofructose units are converted, with ring opening, into dicarboxy(hydroxyethoxy) ethyleneoxy units. The oxidation can proceed in one step with hypohalite, as described in WO91/17189, or in two steps with periodate and chlorite, as described in WO95/12619. Preferred degrees of oxidation (DO) are in the range of from 20 to 90%, the DO being the (molar) percentage of monosaccharide units converted into the corresponding dicarboxy analogues.

6-Carboxy inulin is a well-known material. It can be obtained by oxidation in accordance with the method of WO 95/07303.

Fructan polycarboxylic acid can be prepared by successive oxidation and carboxyalkylation of the selected starting material. The material can have a DO of from 0.2 to 2.0 and a degree of carboxy-alkyl/-acyl substitution of from 0.2 to 3, preferably from 0.5 to 2.5.

Methods of making suitable carboxylated fructan are described in WO2005/073256A1 and WO2013/117672A1.

Suitable phosphonate chelating agents include ethylene diamine tetra methylene phosphonates, and diethylene triamine penta methylene phosphonates (DTPMP). The phosphonate compounds may be present either in their acid form or as salts of different cations on some or all of their acid functionalities. Preferred phosphonate chelating agent to be used herein is diethylene triamine penta methylene phosphonate (DTPMP). Such phosphonate chelating agents are commercially available from Monsanto under the trade name DEQUEST®. Other suitable phosphonate chelating agents include:

a) organic phosphonic acids or salts thereof having the formula: $R_1N[CH_2PO_3H_2]_2$, wherein R1 is a: [(lower)alkyl]N[CH$_2$PO$_3$H$_2$]$_2$ or salt thereof, or [(lower)alkyl]N[CH$_2$PO$_3$H$_2$] [(lower)alkylene]N [CH$_2$PO$_3$H$_2$]$_2$ or salt thereof, or [CH$_2$PO$_3$H$_2$] moiety or salt thereof;

b) phosphonocarboxylic acids, or salts thereof, including those of formula (A) and (B):

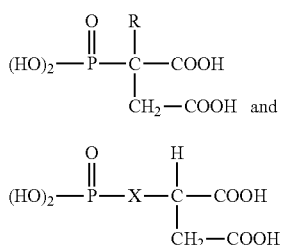

wherein R is hydrogen, alkyl, alkenyl, or alkynyl radical having 1 to 4 carbon atoms, an aryl, cycloalkyl, or aralkyl radical, or the radical selected from the following:

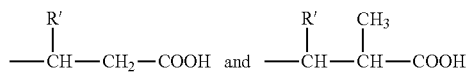

wherein R' is hydrogen, alkyl radical of 1 to 4 carbon atoms, or a carboxyl radical; and X is selected from the following:

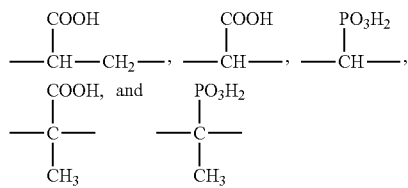

wherein the —PO$_3$H$_2$ group is the phosphono group:

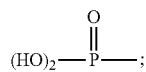

c) and mixtures thereof.

Suitable phosphonate chelating agents are described in EP17150033.3.

A preferred biodegradable chelating agent of use herein is ethylene diamine N,N'-disuccinic acid, or alkali metal, or alkaline earth, ammonium or substitutes ammonium salts thereof or mixtures thereof. Ethylenediamine N,N'-disuccinic acids, especially the (S,S) isomer have been extensively described in U.S. Pat. No. 4,704,233, Nov. 3, 1987, to Hartman and Perkins. Ethylenediamine N,N'-disuccinic acids is, for instance, commercially available under the tradename (S,S)EDDS® from Palmer Research Laboratories. Most preferred biodegradable chelating agent is L-glutamic acid N,N-diacetic acid (GLDA) commercially available under tradename Dissolvine 47S from Akzo Nobel.

Suitable amino carboxylates of use herein include ethylene diamine tetra acetates, diethylene triamine pentaacetates, diethylene triamine pentaacetate (DTPA), N-hydroxyethylethylenediamine triacetates, nitrilotriacetates, ethylenediamine tetrapropionates, triethylenetetraamine-hexa-acetates, ethanoldiglycines, and methyl glycine diacetic acid (MGDA), both in their acid form, or in their alkali metal, ammonium, and substituted ammonium salt forms. Particularly suitable amino carboxylate to be used herein is propylene diamine tetracetic acid (PDTA) which is, for instance, commercially available from BASF under the trade name Trilon FS® and methyl glycine di-acetic acid (MGDA). Most preferred aminocarboxylate used herein is diethylene triamine pentaacetate (DTPA) from BASF. Further carboxylate chelating agents of use herein include salicylic acid, aspartic acid, glutamic acid, glycine, malonic acid or mixtures thereof.

Cleaning Polymer:

The antimicrobial liquid hard surface cleaning composition may comprise a cleaning polymer. It has been found that the presence of a specific cleaning polymer as described herein, when present, allows further improving the grease removal performance of the liquid composition due to the specific sudsing/foaming characteristics they provide to the composition or their surface modification behaviour.

The polymer can be selected from the group consisting of: a vinylpyrrolidone homopolymer (PVP); a polyethyleneglycol dimethylether (DM-PEG); a vinylpyrrolidone/dialkylaminoalkyl acrylate or methacrylate copolymers; a polystyrenesulphonate polymer (PSS); a poly vinyl pyridine-N-oxide (PVNO); a polyvinylpyrrolidone/vinylimidazole copolymer (PVP-VI); a polyvinylpyrrolidone/polyacrylic acid copolymer (PVP-AA); a polyvinylpyrrolidone/vinylacetate copolymer (PVP-VA); a polyacrylic polymer or polyacrylicmaleic copolymer; and a polyacrylic or polyacrylic maleic phosphono end group copolymer; a polyethyleneimine polymer such as carboxylated polyethyleineimine; and mixtures thereof.

Polyethyleneimine polymers such as carboxylated polyethyleineimine are particularly preferred. Suitable polyethyleineimine polymers may be linear or branched, charged or uncharged. They may be hyperbranched or have a dendritic form. They may contain primary, secondary, and/or tertiary amino groups. They are carboxylated by reaction with fatty acids, carboxylic acid and/or carboxylic acid derivatives (such as acrylic acid, maleic acid, maleic anhydride, etc.). They may be alkoxylated, amidated, etc. They may be amphiphilic, amphoteric, alkoxylated, etc. In some embodiments, they may have molecular weights of from about 300 to about 2,000,000. Examples of suitable polyethyleineimine polymers include materials sold by BASF under the trade name Lupasol® and by Nippon Shokubai under the trade name EPOMIN. Examples include Lupasol® FG, Lupasol® G 20, Lupasol® G 35, Lupasol® G 100, Lupasol® G 500, Lupasol® HF, Lupasol® P, Lupasol® PS, Lupasol® PR 8515, Lupasol® WF, Lupasol® FC, Lupasol® PE, Lupasol® HEO 1, Lupasol® PN 50, Lupasol® PN 60, Lupasol® PO 100, Lupasol® SK, etc.

The antimicrobial liquid hard surface cleaning composition may comprise the polymer, especially the polyethyleneimine polymer, at a level of from 0.005% to 2.0%, preferably from 0.1% to 0.5% by weight of the total composition.

Branched Fatty Alcohol:

The liquid hard surface cleaning composition may comprise a branched fatty alcohol, particularly as suds suppressors. Suitable branched fatty alcohols include the 2-alkyl alkanols having an alkyl chain comprising from 6 to 16, preferably from 7 to 13, more preferably from 8 to 12, most preferably from 8 to 10 carbon atoms and a terminal hydroxy group, said alkyl chain being substituted in the a position (i.e., position number 2) by an alkyl chain comprising from 1 to 10, preferably from 2 to 8 and more preferably 4 to 6 carbon atoms. Such suitable compounds are commercially available, for instance, as the Isofol® series such as Isofol® 12 (2-butyl octanol) or Isofol® 16 (2-hexyl decanol) commercially available from Sasol Typically, the liquid hard surface cleaning composition may comprise up to 2.0% by weight of the total composition of said branched fatty alcohol, preferably from 0.10% to 1.0%, more preferably from 0.1% to 0.8% and most preferably from 0.1% to 0.5%.

Solvent:

The liquid hard surface cleaning compositions preferably comprises a solvent. Suitable solvents may be selected from the group consisting of: ethers and diethers having from 4 to 14 carbon atoms; glycols or alkoxylated glycols; alkoxylated aromatic alcohols; aromatic alcohols; alkoxylated aliphatic alcohols; aliphatic alcohols; $C_8$-$C_{14}$ alkyl and cycloalkyl hydrocarbons and halohydrocarbons; $C_6$-$C_{16}$ glycol ethers; terpenes; and mixtures thereof.

Solfactants: The antimicrobial liquid composition may comprise solfactants, i.e. compounds having efficacy as both solvents and surfactants. Suitable solfactants include but are not limited to glycerin ether ethoxylate solfactants of the formula:

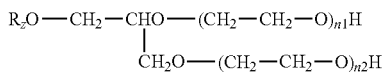

wherein $R_z$ is a linear or branched alkyl group having 1 to 30 carbon atoms, wherein $n_1$ and/or $n_2$ is 1 to 20. Suitable solfactants are described in US 2014/0005273 A1.

Perfumes:

The liquid hard surface cleaning compositions preferably comprise a perfume. Suitable perfumes provide an olfactory aesthetic benefit and/or mask any "chemical" odour that the product may have.

Other Optional Ingredients:

The liquid hard surface cleaning compositions may comprise a variety of other optional ingredients depending on the technical benefit aimed for and the surface treated. Suitable optional ingredients of use herein include builders, other polymers, buffers, bactericides, hydrotropes, colorants, stabilisers, radical scavengers, abrasives, soil suspenders, brighteners, anti-dusting agents, dispersants, dye transfer inhibitors, pigments, silicones and/or dyes.

Wipe or Pad:

The antimicrobial liquid hard surface cleaning composition can also be comprised in an article of manufacture. For instance, the composition can be comprised in a spray dispenser, or in a wipe or pad. Suitable wipes can be fibrous. Suitable fibrous wipes can comprise polymeric fibres, cellulose fibres, and combinations thereof. Suitable cellulose-based wipes include kitchen wipes, and the like. Suitable polymeric fibres include polyethylene, polyester, and the like. Polymeric fibres can be spun-bonded to form the wipe. Methods for preparing thermally bonded fibrous materials are described in U.S. application Ser. No. 08/479,096 (Richards et al.), filed Jul. 3, 1995 (see especially pages 16-20) and U.S. Pat. No. 5,549,589 (Homey et al.), issued Aug. 27, 1996 (see especially Columns 9 to 10). Suitable pads include foams and the like, such as HIPE-derived hydrophilic, polymeric foam. Such foams and methods for their preparation are described in U.S. Pat. No. 5,550,167 (DesMarais), issued Aug. 27, 1996; and commonly assigned U.S. patent application Ser. No. 08/370,695 (Stone et al.), filed Jan. 10, 1995.

Method of Cleaning and Disinfecting a Surface:

The antimicrobial liquid hard surface cleaning compositions described herein are particularly suited for cleaning and disinfecting surfaces selected from the group consisting of: glazed or non-glazed ceramic tiles, enamel, stainless steel, Inox®, Formica®, vinyl, no-wax vinyl, linoleum, melamine, glass, plastics and plastified wood, and combinations thereof. In particular, the compositions are particularly suited for reducing or removing antimicrobial activity from the surface, while also removing greasy residues such as greasy soap scum.

For general cleaning and disinfection, especially of floors, bathroom surfaces, and the like, the preferred method of cleaning comprises the step of:

a) applying the diluted composition to a hard surface.

If desired, the antimicrobial liquid hard surface cleaning composition may be diluted before application, for instance, to a level of from 0.3% to 1.5% by volume. The liquid hard surface cleaning composition may be diluted to a level of from 0.4% to 0.6% by volume, especially where the liquid hard surface cleaning composition has a total surfactant level of greater than or equal to 5% by weight. Where the liquid hard surface cleaning composition has a total surfactant level of less than 5% by weight, the liquid hard surface cleaning composition may be diluted to a level of from 0.7% to 1.4% by volume. In preferred embodiments, the liquid hard surface cleaning composition is diluted with water.

The dilution level is expressed as a percent defined as the fraction of the liquid hard surface cleaning composition, by volume, with respect to the total amount of the diluted composition. For example, a dilution level of 5% by volume is equivalent to 50 ml of the liquid hard surface cleaning composition being diluted to form 1000 ml of diluted composition.

The diluted composition can be applied by any suitable means, including using a mop, sponge, or other suitable implement.

The hard surface may be rinsed, preferably with clean water, in an optional further step, and also as a further step, wiped, such as with a cloth.

More preferably, and especially for particularly dirty or greasy spots, or spots which have been contacted by microbes, the antimicrobial liquid hard surface cleaning compositions, can be applied neat to the hard surface. The compositions described herein provide improved removal of greasy stains, while minimizing the impact on disinfection efficacy.

By "neat", it is to be understood that the liquid composition is applied directly onto the surface to be treated without undergoing any significant dilution, i.e., the liquid composition herein is applied onto the hard surface as described herein, either directly or via an implement such as a sponge, without first diluting the composition. By significant dilution, what is meant is that the composition is diluted by less than 10 wt %, preferably less than 5 wt %, more preferably less than 3 wt %. Such dilutions can arise from the use of damp implements to apply the composition to the hard surface, such as sponges which have been "squeezed" dry.

In another preferred embodiment of the present invention said method of cleaning a hard surface includes the steps of applying, preferably spraying, said liquid composition onto said hard surface, leaving said liquid composition to act onto said surface for a period of time to allow said composition to act, with or without applying mechanical action, and optionally removing said liquid composition, preferably removing said liquid composition by rinsing said hard surface with water and/or wiping said hard surface with an appropriate instrument, e.g., a sponge, a paper or cloth towel and the like.

Methods:

A) pH Measurement:

The pH is measured on the neat composition, at 25° C., using a Sartarius PT-10P pH meter with gel-filled probe (such as the Toledo probe, part number 52 000 100), calibrated according to the instructions manual.

B) Greasy Residue Removal:

White enamel tiles (7 cm×25 cm, supplied by Emaillerie Belge SA) are used in this method. The tiles are soaked in a diluted All Purpose Cleaning composition which is free of surface modification polymers (such as current market European Mr. Propre APC liquid diluted to 2.4 volume %) overnight and rinsed thoroughly the day after with demineralised water to remove all product residues. The tiles are then completely dried.

Greasy soap scum was used as the exemplary greasy residue. Greasy soap scum is prepared by adding 18 g of Artificial Body Soil produced (ABS, supplied by Empirical Manufacturing Company, 7616 Reinhold drive, Cincinnati Ohio 45237 USA) to 240 g of isopropanol, under rapid stirring, before slowly adding 27 g of calcium stearate and then 2.4 g of House Wife Soil with Carbon Black ("HWS", supplied by Warwick Equest Limited, Consett Business Park, 55, Consett DH8 6BN, United Kingdom), and then stirring for 30 minutes while sealed.

The greasy soap scum suspension is then uniformly sprayed onto the enamel tiles using a manual sprayer until 0.3+/−0.5 g of the greasy soap scum (weight after evaporation of the isopropanol) is applied uniformly to each tile. The tiles are placed, flat, in an oven preheated to 140° C. for 30 minutes to evaporate off the isopropanol. If the mass of greasy soap scum on the tile, after evaporation of the isopropanol, is not in the range 0.3+/−0.5 g the tile is discarded and a new tile is prepared using the above procedure.

ENKA Z sponges (16 cm×12 cm yellow viscose sponges, reinforced with cotton, sold by Vileda) are washed 3 times in a washing machine at 96° C. (nil-detergent). Four sponges having a size of 9.0 cm×4.0 cm are cut from the ENKA Z sponges, and then rinsed under running water and squeezed dry. The weight of the four squeezed sponge should be the same (+/−2 g). 5 ml of the test liquid hard surface cleaning composition are applied to the sponge using a pipette.

Applying uniform pressure of 1.4 kN/m², wipe the tile in a linear motion over the tile at a frequency of 20 strokes per minute. This is preferably done using a mechanical apparatus which applies uniform pressure while wiping over the tile length at the defined number of cycles per minute. The number of strokes required to clean the tile is counted. The cleaning test is repeated at least eight times and the result averaged.

The grease soap scum removal index is calculated relative to the reference as follows:

$$\frac{Av.\ \text{number of strokes to clean the tile using the composition}}{Av.\ \text{number of strokes to clean the tile using the reference composition}} \times 100$$

Hence, a lower grade indicates improved polymerized grease cleaning.

C) Shine:

The shine test is done with a soil mixture which consists of a mixture of consumer relevant soils such as oil, polymerized oil, particulates, pet hair, granulated sugar etc. The black glossy ceramic tiles (Black Glossy Sphinx ceramic tiles 20×25 cm, Ref H07300, available at Carobati, Boomsesteenweg 36, 2630 Aartselaar www.carobati.be) are soiled with 0.03 g soil mixture (18.01 wt % Crisco oil [purchased from a North American supermarket], 2.08 wt % of polymerized Crisco oil [polymerized by pumping air at 1 PSI (0.0689 bar) through 500 g of Crisco oil in a 2 L beaker, while stirring at 125 rpm on a hot-plate set at 204° C. for 67 hours, before covering with an aluminum foil and leaving at 204° C. for an additional 30 hours, then cooling to room temperature with hot-plate turned off for 64 hours before heating at 204° C. for 64 hours, before cooling at room temperature with the hot-plate turned off for an additional 24 hours, so that the final viscosity of the oil is between 1800 and 2200 cps, when measured using a Brookfield DVT with spindle nr. 31 at 6 rpm], 28.87 wt % of granulated sugar, and 51.04 wt % of vacuum cleaner soil ["Vacuum Cleaner Soil" supplied by Chem-Pack, 2261 Spring Grove Avenue, Cincinnati Ohio 45214 USA]) by blending the soil mixture with isopropyl alcohol at 1.45 wt % and spraying onto the tile.

The tiles are then cleaned with the liquid hard surface cleaning composition which has been diluted to a level of 0.48 wt % using water having a hardness of 0.93 mmol/l, using a non-woven cloth soaked in the diluted cleaning solution, and wiping first horizontally, then vertically, and then again horizontally. The cloth is then rinsed in the diluted liquid hard surface cleaning composition, and the tiles cleaned in the same manner, using the other side of the nonwoven cloth.

After letting the tiles dry, the tiles are then graded using the grading scale described below, versus tiles cleaned using the reference composition. A positive value means improved shine versus the reference, a negative value means worse shine versus the reference.

Shine Grading Scale:

(average of 3 graders, each grading 2 sets of tiles per product comparison, for a total of six gradings):

0=I see no difference

1=I think there is difference

2=I am sure there is a slight difference

3=I am sure there is a difference

4=I am sure there is a big difference

The shine gradings were averaged to provide the final shine grading.

EXAMPLES

The following compositions were made by simple mixing, with examples 1 to 3 being of the invention and example A being a comparative reference. All the compositions comprised a total of 7.0 wt % of surfactant.

| | Ex A* wt % | Ex 1 wt % | Ex 2 wt % | Ex 3 wt % |
|---|---|---|---|---|
| C10 EO8[1] | 6.6 | 4.9 | 3.4 | 3.4 |
| Polycarboxylated anionic surfactant[2] | 0 | 0 | 1.5 | 1.5 |
| C12-14 amine oxide[3] | 0.4 | 0.1 | 0.1 | 0.1 |
| N-octyl-2-pyrrolidone[4] | 0 | 2.0 | 2.0 | 2.0 |
| DTPA[5] | 0.1 | 0.1 | 0.1 | 1.0 |
| Sodium carbonate | 0.55 | 0.55 | 0.55 | 0.55 |
| DDAC[6] | 0.5 | 0.5 | 0.5 | 0.5 |
| Citric acid | to pH 11 | to pH 11 | to pH 11 | to pH 11 |
| Greasy soap scum removal | 100* | 153 | 185 | 250 |

*Comparative reference
[1]nonionic surfactant commercially available from Sasol
[2]supplied under the trade name Plurafac™ CS-10, by BASF
[3]amine oxide nonionic surfactant, supplied by Huntsman
[4]supplied under the trade name Surfadone™ LP-100 by Ashland
[5]diethylene triamine pentaacetic acid, an aminocarboxylate chelant supplied by Dow chemical
[6]didecyl dimethyl ammonium chloride, supplied under the trade name Bardac 2280 by Lonza As can be seen from the comparing the greasy soap scum removal results from example 1 with comparative example A, replacing part of the surfactant with an alkyl pyrrolidone surfactant resulted in a substantial and unexpected improvement in greasy soap scum removal, even though the composition had an alkaline pH. As can be seen from comparing example 2 with example 1, a further improvement in greasy soap scum removal is achieved when part of the surfactant system is replaced with a polycarboxylated anionic surfactant, even in the presence of a cationic antimicrobial agent. As can be seen from comparing the greasy soap scum removal from example 3 with that from example 2, increasing the chelant level further improves the greasy soap scum removal benefit.

The following compositions of the present invention were made by simple mixing:

| | Ex 4 wt % | Ex 5 wt % | Ex 6 wt % |
|---|---|---|---|
| C9/11 EO8[1] | 5.57 | 3.67 | 3.67 |
| Polycarboxylated anionic surfactant[2] | 0 | 1.9 | 1.9 |
| C12-14 Amine oxide[3] | 0.1 | 0.1 | 0.1 |
| N-Octyl-2-Pyrrolidone[4] | 2.0 | 2.0 | 2.0 |
| Polyethyleneimine polymer[7] | 0 | 0 | 0.2 |
| Carboxylated fructan[8] | 0.1 | 0.1 | 0.1 |
| Sodium carbonate | 0.1 | 0.1 | 0.1 |
| Monoethanolamine | 0.43 | 0.43 | 0.43 |
| Citric acid | 0.3 | 0.3 | 0.3 |
| DDAC | 0.5 | 0.5 | 0.5 |
| Perfume | 0.43 | 0.43 | 0.43 |
| pH | to 10.8 | to 10.8 | to 10.8 |
| Shine grading | Ref | +2.5 | +3.4 |

[7]carboxylated polyethyleineimine, sold under the tradename of Lupasol™ PN60, by BASF
[8]sold under the tradename of Dequest™ FS 1502 by Italmatch Comparing the resultant shine from the composition of example 5 with example 4, replacing part of the surfactant system with a polycarboxylated anionic surfactant results in improved shine of the treated surface. As can be seen from comparing the shine results from example 6 with example 5, the addition of a polyethyleneimine polymer results in further improvements in shine.

The following compositions of the present invention were made by simple mixing:

| | Ex 7 wt % | Ex 8 wt % |
|---|---|---|
| C9/11 EO8[1] | 5.57 | 5.57 |
| Polycarboxylated anionic surfactant[2] | 0 | 0.1 |
| C12-14 Amine oxide[3] | 0.1 | 0.1 |
| N-Octyl-2-Pyrrolidone[4] | 2.0 | 2.0 |
| Polyethyleneimine polymer[7] | 0 | 0.1 |
| Carboxylated fructan[8] | 0 | 0 |
| Sodium carbonate | 0.1 | 0.1 |
| Monoethanolamine | 0.43 | 0.43 |
| Citric acid | 0.3 | 0.3 |
| DDAC[6] | 0.7 | 0.7 |
| Perfume | 0.43 | 0.43 |
| pH | to 10.8 | to 10.8 |
| Shine grading | Ref | +2.0 |

Comparing the resultant shine from the composition of example 8 with example 7, the shine benefit from the polycarboxylated anionic surfactant and polyethyleneimine polymer are maintained even at higher levels of the antimicrobial agent.

The following are further examples of the present invention:

| | Ex 10 wt % | Ex 11 wt % | Ex 12 wt % | Ex 13 wt % | Ex 14 wt % | Ex 15 wt % | Ex 16 wt % | Ex 17 wt % |
|---|---|---|---|---|---|---|---|---|
| C9/11 EO8[1] | 0.97 | 0.1 | 3.0 | 2.00 | 6.20 | 4.20 | 0 | 4.00 |
| Alkyl polyglycoside[9] | 0 | 0 | 1.5 | 0 | 0 | 0 | 5.7 | 0 |
| Polycarboxylated anionic surfactant[2] | 0.25 | 0 | 0 | 0 | 3.0 | 1.5 | 1.0 | 0 |
| Alkyl ether carboxyalte[10] | 0 | 0.25 | 0 | 0 | 0 | 0 | 0 | 1.0 |
| Alkylpolyglucoside esters[11] | 0 | 0 | 0.75 | 0 | 0 | 0 | 0.50 | 0 |
| DTPA[3] | 0 | 0.1 | 0 | 0.1 | 0 | 1.0 | 0.1 | 0 |
| GLDA[12] | 0.1 | 0 | 0 | 0 | 0 | 0 | 0 | 2.0 |
| 2-Phosphonobutane-1,2,4-tricarboxylic acid[13] | 0 | 0 | 0.3 | 0 | 0.1 | 0 | 0 | 0 |
| Sodium carbonate | 0.017 | 0.1 | 0.25 | 0.10 | 0.55 | 0.1 | 0.4 | 0.1 |
| Monoethanolamine | 0.75 | 0.9 | 0.45 | 0.50 | 0 | 0.75 | 0.50 | 1.5 |
| N-Octyl-2-Pyrrolidone[4] | 0.33 | 0.15 | 0.85 | 1.00 | 3.00 | 2.00 | 1.50 | 2.00 |
| C12-14 Amine oxide[5] | 0.055 | 0.5 | 0 | 1.00 | 1.50 | 0.40 | 3.50 | 0 |
| C10-C18 Alkyl dimethyl carboxymethyl betaine | 0 | 0 | 0 | 0 | 0 | 0 | 0 | 2.00 |
| Citric acid | 0.05 | 0 | 0.55 | 0.30 | 0 | 0.10 | 0.15 | 0 |
| n-BPP[14] | 0 | 0 | 0 | 0 | 0 | 2.00 | 0 | 0 |
| Polyethyleneimine polymer[7] | 0.05 | 0 | 0.15 | 0 | 0 | 0.3 | 0 | 0.25 |
| Carboxylated fructan[8] | 0 | 0 | 0 | 0 | 0.1 | 0 | 0.1 | 0 |

-continued

|  | Ex 10 wt % | Ex 11 wt % | Ex 12 wt % | Ex 13 wt % | Ex 14 wt % | Ex 15 wt % | Ex 16 wt % | Ex 17 wt % |
|---|---|---|---|---|---|---|---|---|
| DDAC[6] | 0.1 | 0.15 | 0.75 | 0.25 | 0 | 0.9 | 0.65 | 0 |
| C12-C18, dimethyl ethylbenzyl ammonium chloride[15] | 0 | 0 | 0 | 0 | 1.0 | 0 | 0 | 0.75 |
| Perfume | 0.10 | 0.15 | 0.70 | 0.35 | 1.0 | 1.0 | 0.80 | 0.60 |
| Polymeric thickener[6] | 0 | 0 | 0 | 0 | 0.97 | 0.97 | 0 | 0 |
| NaOH to pH | 11.1 | 11.0 | 10.8 | 10.5 | 10.3 | 10.8 | 10.8 | 11.1 |

[9]Glucopon™ 425N, supplied by BASF
[10]Empicol CED5, supplied by Huntsman
[11]Eucarol AGE EC, supplied by Lamberti
[12]Tetra sodium salt of glutamic acid diacetic acid, supplied under the tradename of Dissolvine™ 47S by Akzo Nobel
[13]Bayhibit AM, supplied by Lanxess
[14]Dipropylene glycol n-butyl ether
[15]Supplied under the trade name Barquat 4280Z by Lonza The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An antimicrobial liquid hard surface cleaning composition comprising:
   (a) an alkylpyrrolidone surfactant, wherein the alkyl pyrrolidone is present at a level of from 0.1 to 10% by weight of the composition;
   (b) additional nonionic surfactant, wherein the additional nonionic surfactant is present at a level of from 0.3% to 12% by weight of the antimicrobial liquid hard surface cleaning composition, and wherein the additional nonionic surfactant comprises alkoxylated nonionic surfactants and amine oxide nonionic surfactant, such that the antimicrobial liquid hard surface cleaning composition comprises:
      (i) from 0.27% to 8.0% by weight of the antimicrobial liquid hard surface cleaning composition of alkoxylated nonionic surfactant; and
      (ii) from 0.03% to 4.0% by weight of the composition of amine oxide surfactant;
   (c) an antimicrobial agent; and
   (d) a polyethyleneimine polymer;
   wherein the liquid hard surface cleaning composition has a pH of greater than 4.0.

2. The antimicrobial liquid hard surface cleaning composition according to claim 1, wherein the alkyl pyrrolidone is a C5-C12 alkyl pyrrolidone.

3. The antimicrobial liquid hard surface cleaning composition according to claim 1, wherein the antimicrobial agent is selected from the group consisting of: quaternary ammonium compounds and mixtures thereof.

4. The antimicrobial liquid hard surface cleaning composition according to claim 1, wherein the antimicrobial liquid hard surface cleaning composition comprises the antimicrobial agent at a level of from 0.01 to 2.0% by weight of the antimicrobial liquid hard surface cleaning composition.

5. The antimicrobial liquid hard surface cleaning composition according to claim 1, wherein the antimicrobial liquid hard surface cleaning composition comprises polycarboxylated surfactant.

6. The antimicrobial liquid hard surface cleaning composition according to claim 5, wherein the polycarboxylated surfactant is present at a level of from 0.05% to 5% by weight of the antimicrobial liquid hard surface cleaning composition.

7. The antimicrobial liquid hard surface cleaning composition according to claim 1, wherein the polyethyleneimine polymer is present at a level of from 0.005% to 2.0% by weight of the total antimicrobial liquid hard surface cleaning composition.

8. The antimicrobial liquid hard surface cleaning composition according to claim 1, wherein the antimicrobial liquid hard surface cleaning composition further comprises a chelant, selected from the group consisting of: amino-carboxylates carboxylated fructan, phosphonate chelating agents, and mixtures thereof.

9. The antimicrobial liquid hard surface cleaning composition according to claim 8, wherein the antimicrobial liquid hard surface cleaning composition comprises the chelant at a level of from 0.025% to 5.0% by weight of the antimicrobial liquid hard surface cleaning composition.

10. The antimicrobial liquid hard surface cleaning composition according to claim 1, wherein the composition has a pH of from 4.0 to 13 measured on the neat antimicrobial liquid hard surface cleaning composition, at 25° C.

* * * * *